(12) United States Patent
Von Gunten et al.

(10) Patent No.: US 9,522,184 B2
(45) Date of Patent: Dec. 20, 2016

(54) CD89 ACTIVATION IN THERAPY

(75) Inventors: Stephan Von Gunten, Bern (CH); Marc Wehrli, Bern (CH); Adrian Zürcher, Bern (CH); Sylvia Miescher, Bern (CH)

(73) Assignees: CSL BEHRING AG, Bern (CH); UNIVERSITAT BERN, Bern (CH)

( * ) Notice: Subject to any disclaimer, the term of this patent is extended or adjusted under 35 U.S.C. 154(b) by 138 days.

(21) Appl. No.: 13/991,811

(22) PCT Filed: Dec. 14, 2011

(86) PCT No.: PCT/EP2011/072711
§ 371 (c)(1),
(2), (4) Date: Jul. 12, 2013

(87) PCT Pub. No.: WO2012/080306
PCT Pub. Date: Jun. 21, 2012

(65) Prior Publication Data
US 2013/0302345 A1 Nov. 14, 2013

(30) Foreign Application Priority Data
Dec. 14, 2010 (EP) .................................... 10194942

(51) Int. Cl.
A61K 39/395 (2006.01)
C07K 16/28 (2006.01)

(52) U.S. Cl.
CPC .......... A61K 39/3955 (2013.01); C07K 16/283 (2013.01); C07K 2317/73 (2013.01); C07K 2317/75 (2013.01)

(58) Field of Classification Search
None
See application file for complete search history.

(56) References Cited

U.S. PATENT DOCUMENTS 6,300,104 B1 * 10/2001 Morrison et al. .......... 435/70.21
6,967,106 B2 * 11/2005 Simon ........................... 436/513

FOREIGN PATENT DOCUMENTS

| WO | WO 95/04081 A1 | 2/1995 |
| WO | WO 2004/012763 A1 | 2/2004 |
| WO | WO 2005/047337 A1 | 5/2005 |

OTHER PUBLICATIONS

Schettini et al., J Leukoc Biol. Oct. 2002;72(4):685-91.*
Janheway et al., Immunobiology, 3rd edition, 1997, Garland Publishing Inc., pp. 9:19-9:20.*
Janeway et al, Immunobiology, 3rd edition, 1997, Garland Publishing, pp. 8:18 to 8:19.*
Communication Pursuant to Article 94(3) EPC issued Dec. 15, 2014, in European Patent Application No. 11794757.2.
Communication Pursuant to Article 94(3) EPC issued Apr. 23, 2014, in European Patent Application No. 11794757.2.
Chinese Office Action and Search Report with English translations thereof, dated May 6, 2014, for Chinese Application No. 201180060034.4.
Extended European Search Report for European Application No. 10194942.8 dated Oct. 28, 2011.
International Search Report and Written Opinion of the International Searching Authority (Forms PCT/ISA/220, PCT/ISA/210 and PCT/ISA/237) for International Application No. PCT/EP2011/072711 dated May 16, 2012.
Kanamaru et al., "IgA Fc receptor I signals apoptosis through the FcRγ ITAM and affects tumor growth," Blood, vol. 109, No. 1, Jan. 1, 2007 (Prepublished online: Sep. 21, 2006), pp. 203-211.
Krajci et al., "Molecular Cloning of the Human Transmembrane Secretory Component (POLY-lg Receptor) and its mRNA Expression in Human Tissues," Blochem. Biophys. Res. Comm., vol. 158, No. 3, Feb. 15, 1989, pp. 783-789.
Nicoletti et al., "A rapid and simple method for measuring thymocyte apoptosis by propidium iodide staining and flow cytometry," J. Immunol. Methods, vol. 139, 1991, pp. 271-279.
Pasquier et al., "Identification of FcαRI as an Inhibitory Receptor that Controls Inflammation: Dual Role of FcRγ ITAM," Immunity, vol. 22, Jan. 2005, pp. 31-42.
Pleass et al., "Identification of Residues in the CH2/CH3 Domain Interface of IgA Essential for Interaction with the Human Fcα Receptor (Fc αR) CD89," J. Biol. Chem, vol. 274, No. 33, Aug. 13, 1999, pp. 23508-23514.
Salamone et al., "Promotion of Neutrophil Apoptosis by TNF-α1," J. Immunol, vol. 166, 2001, pp. 3476-3483.
Schettini et al., "Stimulation of neutrophil apoptosis by immobilized IgA," Journal of Leukocyte Biology, vol. 72, Oct. 2002, pp. 685-691.
Takeshita et al., "Intravenous immunoglobulin preparations promote apoptosis in lipopolysaccharide-stimulated neutrophils via an oxygen-dependent pathway in vitro," APMIS, vol. 113, 2005, pp. 269-277.
Van Der Steen et al., "Immunoglobulin A: FcαRI Interactions Induce Neutrophil Migration Through Release of Leukotriene B4," Basic-Alimentary Tract, Gastrogenterology, vol. 137, 2009, pp. 2018-2029.
Von Gunten et al., "Siglec-9 transduces apoptotic and nonapoptotic death signals into neutrophils depending on the proinflammatory cytokine environment," Blood, vol. 106, No. 4, Aug. 15, 2005 (Prepublished online: Apr. 12, 2005), pp. 1423-1431.
Wörn et al., "Stability Engineering of Antibody Single-chain Fv Fragments," J. Mol. Biol, vol. 305, 2001, pp. 989-1010.
Invitation to Respond to Written Opinion issued Oct. 30, 2014, in Singapore Patent Application No. 2013041322.

(Continued)

Primary Examiner — Michael Szperka
(74) Attorney, Agent, or Firm — Birch, Stewart, Kolasch & Birch, LLP

(57) ABSTRACT

The invention relates to the use of CD89 activating molecules, in particular Fc alpha comprising molecules, and more particularly, IgA, for inducing apoptosis in neutrophils. Anti-CD89 antibodies can alternatively be used. The CD89 activation is beneficial in the treatment of various disorders associated with increases in neutrophils, such as autoimmune disorders, inflammatory disorders, NETosis, or cystic fibrosis.

31 Claims, 11 Drawing Sheets

(56) References Cited

OTHER PUBLICATIONS

Wright, H.L. et al, "Neutrophil function in inflammation and inflammatory diseases," Rheumatology, 2010, vol. 49, pp. 1618-1631.
Japanese Office Action for Appl. No. 2013-543743 dated Dec. 1, 2015 (w/ English translation).
De Wit et al., "Structure of the gene for the human myeloid IgA Fc receptor (CD89)," The Journal of Immunology, vol. 155, 1995, pp. 1203-1209.
Boullier, S. et al, "Secretory IgA-Mediated Neutralization of Shigella flexneri Prevents Intestinal Tissue Destruction by Down-Regulating Inflammatory Circuits," the Journal of Immunology, 2009, vol. 183, No. 9, pp. 5879-5885.

\* cited by examiner

Figure 1
Figure 1A
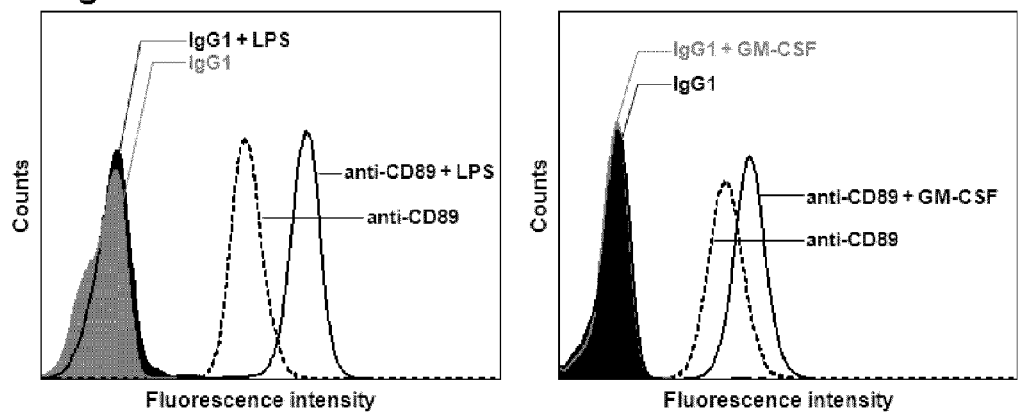
Figure 1B
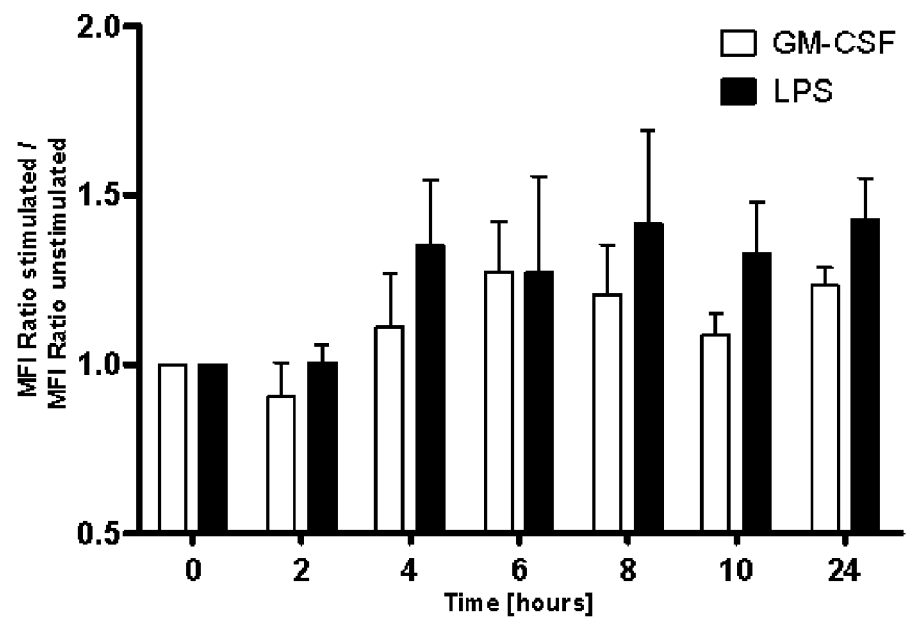

Figure 2
Figure 2A
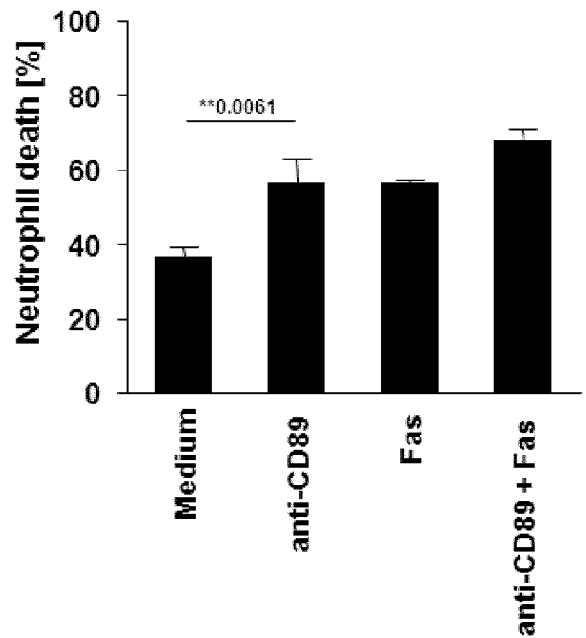
Figure 2B
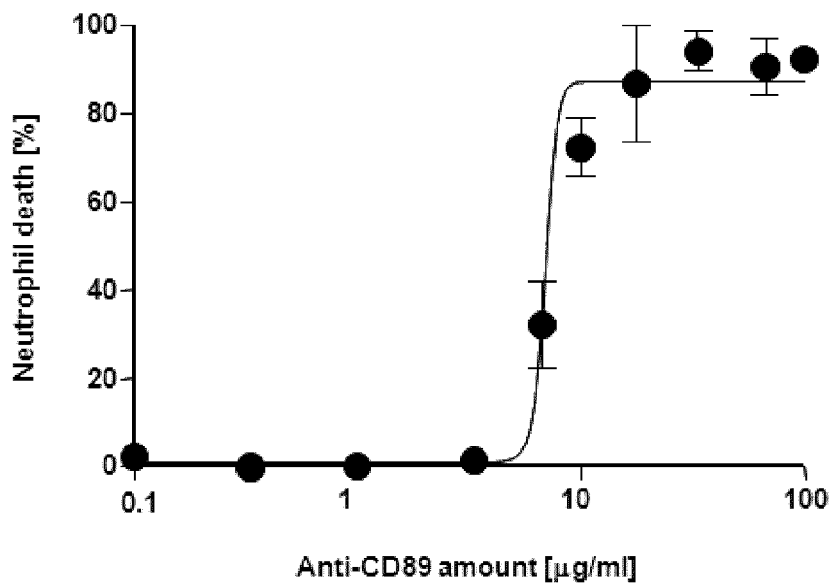

SEQUENCE LISTING

```
<160> NUMBER OF SEQ ID NOS: 2

<210> SEQ ID NO 1
<211> LENGTH: 687
<212> TYPE: DNA
<213> ORGANISM: Homo sapiens

<400> SEQUENCE: 1
ccccgactgt cactgcaccg accggccctc gaggacctgc tcttaggttc agaagcgaac      60
ctcacgtgca cactgaccgg cctgagagat gcctcaggtg tcaccttcac ctggacgccc     120
tcaagtggga agagcgctgt tcaaggacca cctgaccgtg acctctgtgg ctgctacagc     180
```

```
gtgtccagtg tcctgtcggg ctgtgccgag ccatggaacc atgggaagac cttcacttgc     240
actgctgcct accccgagtc caagacsccg ctaaccgcca ccctctcaaa atccggaaac     300
acattccggc ccgaggtcca cctgctgccg ccgccgtcgg aggagctggc cctgaacgag     360
ctggtgacgc tgacgtgcct ggcacgtggc ttcagcccca aggatgtgct ggttcgctgg     420
ctgcaggggt cacaggagct gccccgcgag aagtacctga cttgggcatc ccggcaggag     480
cccagccagg gcaccaccac cttcgctgtg accagcatac tgcgcgtggc agccgaggac     540
tggaagaagg gggacacctt ctcctgcatg gtgggccacg aggccctgcc gctggccttc     600
acacagaaga ccatcgaccg cttggcgggt aaacccaccc atgtcaatgt gtctgttgtc     660
atggcggagg tggacggcac ctgctac                                         687

<210> SEQ ID NO 2
<211> LENGTH: 687
<212> TYPE: DNA
<213> ORGANISM: Homo sapiens

<400> SEQUENCE: 2
ccccgactgt cgctgcaccg accggccctc gaggacctgc tcttaggttc agaagcgaac      60
ctcacgtgca cactgaccgg cctgagagat gcctctggtg ccaccttcac ctggacgccc     120
tcaagtggga agagcgctgt tcaaggacca cctgagcgtg acctctgtgg ctgctacagc     180
gtgtccagtg tcctgcctgg ctgtgccag ccatggaacc atggggagac cttcacctgc     240
actgctgccc accccgagtt gaagacccca ctaaccgcca acatcacaaa atccggaaac     300
acattccggc ccgaggtcca cctgctgccg ccgccgtcgg aggagctggc cctgaacgag     360
ctggtgacgc tgacgtgcct ggcacgtggc ttcagcccca aggatgtgct ggttcgctgg     420
ctgcaggggt cacaggagct gccccgcgag aagtacctga cttgggcatc ccggcaggag     480
cccagccagg gcaccaccac cttcgctgtg accagcatac tgcgcgtggc agccgaggac     540
tggaagaagg gggacacctt ctcctgcatg gtgggccacg aggccctgcc gctggccttc     600
acacagaaga ccatcgaccg cttggcgggt aaacccaccc atgtcaatgt gtctgttgtc     660
atggcggagg tggacggcac ctgctac                                         687
```

CD89 ACTIVATION IN THERAPY

The invention relates to the use of CD89 activating molecules, in particular Fc alpha comprising molecules, and more particularly, IgA, for inducing apoptosis in neutrophils. Anti-CD89 antibodies can alternatively be used. The CD89 activation is beneficial in the treatment of various disorders associated with increases in neutrophils, such as autoimmune disorders, inflammatory disorders, NETosis, or cystic fibrosis.

Neutrophils form an essential part of the innate immune system. They are normally found in the blood stream. During the acute phase of inflammation, e.g. as a result of a bacterial infection, neutrophils migrate towards the site of inflammation by chemotaxis, attracted by cytokines/chemokines released by activated endothelium, mast cells and macrophages at the site of infection or inflammation. Neutrophils also express and release cytokines, which amplify inflammatory reactions by other cell types. Neutrophils play a key role in the defense against invading pathogens, using phagocytosis, degranulation, thereby releasing soluble anti-microbial agents, and the generation of neutrophil extracellular traps (NETs), which comprise a web of fibres composed of chromatin and granule proteins such as serine proteases that trap and kill microbes extracellularly. NETs may also trap the pathogens and prevent their further spread. Neutrophils will often be phagocytosed themselves by macrophages.

Immunoglobulin A (IgA) is the prominent antibody class at mucosal surfaces, where it represents the key player of adaptive mucosal immunity. Diseases associated with total or partial lack of IgA, such as common variable immunodeficiency (CVID) or complete IgA deficiency, are associated with recurrent sinopulmonary and gastrointestinal infection, bronchiectasis and autoimmune diseases. One common finding in the acute state of these immunopathological conditions is neutrophilic infiltration, which by the release of toxic mediators and catabolic enzymes causes substantial collateral tissue damage. Therefore, while neutrophils have many beneficial functions, they can also cause significant damage if not eliminated effectively when the initial stimulus has been removed.

The IgA receptor CD89 (FcAlphaR) is a transmembrane glycoprotein present on the surface of myeloid lineage cells such as neutrophils, monocytes, macrophages and eosinophils, where it mediates immunologic responses to pathogens. It interacts with IgA-opsonised targets, and triggers immunologic defense processes such as phagocytosis, antibody-dependent cell-mediated cytotoxicity, release of inflammatory mediators and triggering of respiratory burst activity.

The inventors have now surprisingly found that CD89-activation, in particular by Fc-alpha comprising molecules such as IgA or an anti-CD89 antibody, can induce apoptosis in neutrophils, and that this activity is enhanced when neutrophils have been pre-activated with, for example, microbial components such as lipopolysaccharide (LPS) or lipoteichoic acid (LTA), or cytokines such as GM-CSF or TNF-alpha. This observation is highly relevant for the treatment of diseases involving chronic neutrophilic inflammation, e.g. autoimmune inflammatory conditions, conditions involving excessive NETosis, chronic infections with pus formation or conditions of sterile neutrophil-mediated inflammation that may persist or become chronic after resolution of an infection that initially led to recruitment of neutrophils to the site of infection. Therefore, in the present invention, the activation of CD89 actually leads to an inhibition in inflammation, by activation of the apoptotic pathway in neutrophils.

One aspect of the invention is therefore a CD89-activating molecule such as an Fc-alpha-comprising molecule or anti-CD89 antibody for use in inducing apoptosis in neutrophils, preferably in pre-activated neutrophils. Preferably, the Fc-alpha-comprising molecule is immunoglobulin A (IgA). The IgA may be polyclonal, and it may be derived from serum or plasma, preferably from human serum or plasma. The IgA may be, for example, dimeric or monomeric, or a mixture thereof. Dimeric IgA may also comprise a J-chain, and it may additionally comprise a secretory component. The use of monoclonal IgA is also contemplated. The IgA may be IgA1 or IgA2 or a mixture thereof. Preferably the IgA is human, however, primate IgA may also be used. Dimeric IgA from serum or plasma may also be combined with secretory component, preferably recombinant secretory component, even more preferably with human recombinant secretory component. Tetrameric forms of IgA can also occur occasionally.

The Fc-alpha comprising molecule may also be Fc-alpha itself or a functional variant thereof (e.g. a tail-truncated form, lacking some of the C-terminal amino acid residues, for example the 18 C-terminal amino acid residues, see Pleass, R J et al, J. Biol. Chem. 274, 23508-23514, 1999), but preferably it is a fusion protein of the Fc portion of IgA or functional variant thereof with another protein, for example with albumin, such as human serum albumin. However, other soluble proteins can also be used as fusion partners. In addition, single-chain Fc-alpha portions, or single chain versions of a functional variant of Fc-alpha, are contemplated, as well as dimers or even multimers of such single-chain Fc-alpha portions. When we refer to Fc-alpha in this document, functional variants of Fc-alpha, e.g. tail-truncated forms and/or other functional variants, e.g. Fc-alpha molecules with one or more amino acid substitutions, deletions or insertions that do not lead to a loss of CD89-activating activity, are also meant to be encompassed in the term "Fc-alpha".

A functional variant is a molecule that retains at least 30% of the CD89-activating activity of the original molecule, preferably at least 40%, 50%, or 60%, more preferably at least 70%, 75%, 80%, 90%, 95% even more preferably at least 98%, most preferably full activity. It is also contemplated that the functional variant could have enhanced CD89-activating activity.

Anti-CD89 may be an antiserum produced by immunization with CD89 or fragments thereof, purified antibodies or CD89-binding fragments thereof from an anti-CD89 antiserum, or monoclonal anti-CD89 antibodies or CD89-binding fragments thereof. Preferably, a monoclonal anti-CD89 antibody is used. Once a monoclonal antibody with the desired activity is identified, mimetics can be produced that have the same effect as the monoclonal antibody.

Another aspect of the invention is a pharmaceutical composition comprising the CD89-activating molecule, preferably the Fc-alpha-comprising molecule or anti-CD89 antibody described above, wherein at least 50% of the protein in the composition is the Fc-alpha-comprising molecule or anti-CD89 antibody. Preferably, at least 60% of the protein is the Fc-alpha comprising molecule or anti-CD89 antibody, more preferably at least 70%, 75%, 80%, 85%, 90%, or 95%, most preferably at least 98%.

In another aspect of the invention, the neutrophils that are treated with the CD89-activating molecule, preferably the Fc-alpha comprising molecule or anti-CD89 antibody, are located in a patient with an autoimmune disorder or inflammatory condition, in particular chronic neutrophilic inflammatory conditions. Examples of the autoimmune disorder or inflammatory condition are sterile neutrophilic inflammation, such as pleural empyema, or empyema in other cavities such as uterus (pyometra), infectious inflammation e.g. meningitis with pus, Cystic Fibrosis, bronchiectasis, neutrophil-induced inflammation, NETosis, arthritis, in particular rheumatoid arthritis, spondyloarthritis, ankylosing spondylitis/Morbus Bechterew or reactive arthritis (e.g. Reiter's disease). Further examples include other inflammatory conditions which are mainly mediated by neutrophils, such as inflammatory bowel disease (IBD).

In another aspect of the invention, the CD89-activating molecule, preferably the Fc-alpha comprising molecule or the anti-CD89 antibody, is administered locally to the site of increased neutrophil numbers, e.g. into the diseased joint of an arthritis patient, in particular into the diseased joint of a rheumatoid arthritis patient, or to the site of a sterile or infectious inflammation, or to the site of chronic neutrophilic inflammation.

The neutrophils may also be located in the lung of a patient with cystic fibrosis, where NETosis, i.e. excessive NET (neutrophil extracellular trap) formation, has been correlated with impaired obstructive lung function. In this case, it is advantageous to administer the CD89-activating molecule, preferable the Fc-alpha comprising molecule, by inhalation. Preferably, it is administered in combination with DNase.

In addition, the NETosis may be associated with the pathogenesis of other autoinflammatory conditions such as preeclampsia, septic shock and autoimmune vasculitis. Another aspect of the invention is therefore the Fc-alpha comprising molecule, in particular IgA, or anti-CD89 antibody for use in the treatment of these conditions, preferably for use in the induction of apoptosis in neutrophils, preferably in activated neutrophils, located in patients suffering from these conditions.

Another aspect of the invention is a method for inducing apoptosis of neutrophils, comprising bringing the neutrophils in contact with an effective dose of a CD89-activating molecule such as an Fc-alpha comprising molecule or an anti-CD89 antibody. Preferably, the neutrophils have been or are subjected to inflammatory cytokines or microbial products or other stimuli prior or during the contact with the CD89-activating molecule.

The effective dose of an Fc-alpha comprising molecule may be above the concentration of IgA in plasma, preferably about three times the IgA plasma concentration, more preferably about 10 times, 15 times or 20 times, the IgA plasma concentration, or even higher.

The CD89-activating molecule, preferably the Fc-alpha comprising molecule or the anti-CD89 antibody, is preferably comprised in a pharmaceutical composition, comprising one or more pharmaceutically acceptable excipients. The composition may additionally comprise a stabilizer.

The route of administration can be intravenous, subcutaneous, inhaled, intranasal, topical (i.e. skin or mucosal surface including gut or eye, administered as eyedrops), oral, but preferably the administration occurs locally, i.e. to the site of excessive neutrophil infiltration or activity, e.g. into the arthritic joint, by inhalation for cystic fibrosis, by injection to the site of a sterile infection etc. The dosage form may be a tablet, capsule, cream, suppository, but preferably it is a sterile solution. The product may be provided in lyophilized form and reconstituted into liquid form prior to use, or it may be provided as a stable liquid formulation.

Another aspect of the invention is the CD89-activating molecule, such as the Fc-alpha comprising molecule or anti-CD89 antibody, used in combination with other therapeutic agents, such as anti-inflammatory compounds, e.g. NSAIDs, antibodies that can modulate the immune response such as anti-CD20 (e.g. Rituxan), anti-TNFalpha (e.g. Remicade, Humira), antibiotics, anti-viral compounds such as ganciclovir, anti-fungal compounds such as Voriconazol, or anti-protozoan compounds.

The Fc-alpha-comprising molecule may be polyclonal IgA, e.g. isolated from serum or plasma, preferably from human serum or plasma. More preferably, it is purified from a pool of human plasma. Even more preferably, it is purified as a by-product of human plasma fractionation and/or subsequent purification of plasma proteins, most preferably from a side fraction that is produced during the manufacture of IgG preparations (e.g. IVIg or SCIg) from pooled human plasma, and/or from a precipitate obtained during the manufacture of IgG preparations from plasma.

Preferably, the IgA dimers are isolated (or enriched) from human pooled plasma. More preferably, these dimers are further combined with secretory component, e.g. secretory component produced recombinantly. The resulting secretory IgA is likely to be more stable in environments with high level of proteases, e.g. synovial fluid of an arthritic joint or the inflamed lung or gut. As most neutrophil granule proteins are proteases, this may be a particularly preferred way to carry out the present invention.

Alternatively, the IgA may be monoclonal. Monoclonal IgA may be produced by hybridoma cell lines, or by engineered cell lines, comprising the cDNA for the light chain and the heavy chain in an expression plasmid with an appropriate promoter and optionally further regulatory elements. The skilled person is well aware of methods to produce hybridomas, e.g. by cell fusion or immortalization of IgA-producing B-lymphocytes. Methods to isolate the cDNAs encoding the antibody heavy chain and light chain, and clone these cDNAs into appropriate expression vectors are also well known in the art. The expression vectors can then be transfected into cell lines, for example mammalian cell lines such as CHO cells or HEK293 cells, and cell lines can be selected that stably express the desired antibody. Suitable techniques are found, for example, in Current Protocols in Molecular Biology, Ausubel F M et al. (eds.) John Wiley & Sons, Inc. Functional variants of IgA, e.g. IgA with one or more amino acid substitutions, deletions or insertions that do not lead to a loss of CD89-activating activity, are also meant to be encompassed when the term "IgA" is used throughout this document.

The Fc-alpha comprising molecule may also be an engineered fusion protein. For example, the cDNA encoding the Fc-alpha portion of the IgA heavy chain is fused in frame to the cDNA encoding another protein, preferably a soluble protein, for example human serum albumin. Examples of suitable Fc-alpha cDNA sequences are shown in SEQ ID NOs: 1 and 2.

The Fc-alpha comprising molecule may also be a single chain Fc-alpha protein, where two Fc-alpha cDNAs are linked by a nucleic acid encoding a linker peptide, similar to the way single-chain Fv fragments are engineered. (Wörn A, Plückthun A. J. Mol. Biol, 2001; 305:989-1010). Two or more of such single-chain Fc-alpha proteins may also be connected to form a dimer or multimer of Fc-alpha units.

Such molecules can be produced by routine techniques, for example as described in Current Protocols in Molecular Biology, Ausubel F M et al. (eds.) John Wiley & Sons, Inc. For example, the Fc-alpha portion of the IgA heavy chain can be amplified from an IgA producing cell by RT-PCR, using primers designed to contain appropriate restriction sites. The resulting cDNA can then be digested with the corresponding restriction enzyme(s) and cloned into a suitably prepared expression vector. Synthetic oligonucleotides encoding linker peptides can be inserted into the appropriate positions, for example by digesting the cDNA with appropriate restriction enzymes and ligating the oligonucleotides with appropriately designed ends into the vector. The complete expression plasmid can then be produced in large amounts, e.g. in *E. coli*, using standard techniques. After purification, it can be transfected into mammalian cells, and cell lines stably expressing the desired proteins can be produced. The proteins can then be purified. Standard techniques are available to carry out these procedures.

Chimeric Fc-alpha portions, comprising, for example, one constant domain from the heavy chain of IgA1 and one constant domain from the heavy chain of IgA2 are also contemplated; the skilled person is well aware of the immunoglobulin domains and can identify the domain borders and combine immunoglobulin domains as desired. Combinations of Fc-alpha portions with J-chain are also included; additionally the resulting molecule may also be combined with secretory component. As mentioned above, functional fragments of Fc-alpha and functional variants can also be used; fusion proteins, dimers, multimers, combinations of such functional variants with J-chain, or with J-chain and secretory component, are also included.

The preferred secretory component contains at least a segment of the amino acid residues 1 to residue about 606 of the human polymeric immunoglobulin receptor (pIgR) amino acid sequence or variants thereof, e.g. analogous portions from a different mammalian species. However, the human sequence is preferred. The protein sequence of the human pIgR can be found under SwissProt accession number P01833 (see also Krajci et al, 1989, Biochem. Biophys. Res. Comm 158, 783-789).

Alternatively, the CD89 activating protein may be anti-CD89. The skilled person will be well aware of methods to produce anti-CD89. CD89, or fragments thereof, may be used as an antigen to produce a specific antiserum. Antibodies may be isolated from such an antiserum. Monoclonal antibodies may also be produced, and the methods of producing such monoclonal antibodies are well known to the skilled person. Preferably, the monoclonal anti-CD89 antibody is a human antibody, e.g. produced from immortalized human B-lymphocytes or in an animal where the animal's own immunoglobulin genes have been at least partially replaced by the corresponding human genes. The techniques used for the production of antibodies are well known, and are described in detail in various laboratory manuals, e.g. Ed Harlow & David Lane: Antibodies, A Laboratory Manual, or Sambrook et al: Molecular Cloning, A Laboratory Manual (both from CSHL).

BRIEF DESCRIPTION OF THE DRAWINGS

FIG. 1A shows CD89 expressed on human neutrophils assessed by flow cytometry in the presence of LPS (left panel) or GM-CSF (right panel).

FIG. 1B shows time course of CD89 upregulation on human neutrophils with LPS and GM-CSF.

FIG. 2A shows the effect of ligation of CD89 by anti-CD89 monoclonal antibody on neutrophil death in 22 hour culture as compared to medium without anti-CD89, with anti-Fas, and with anti-CD89+anti-Fas.

FIG. 2B shows a concentration curve of anti-CD89 mAb in 22 hour cultures on neutrophil death.

EXAMPLES

Figure 3A:
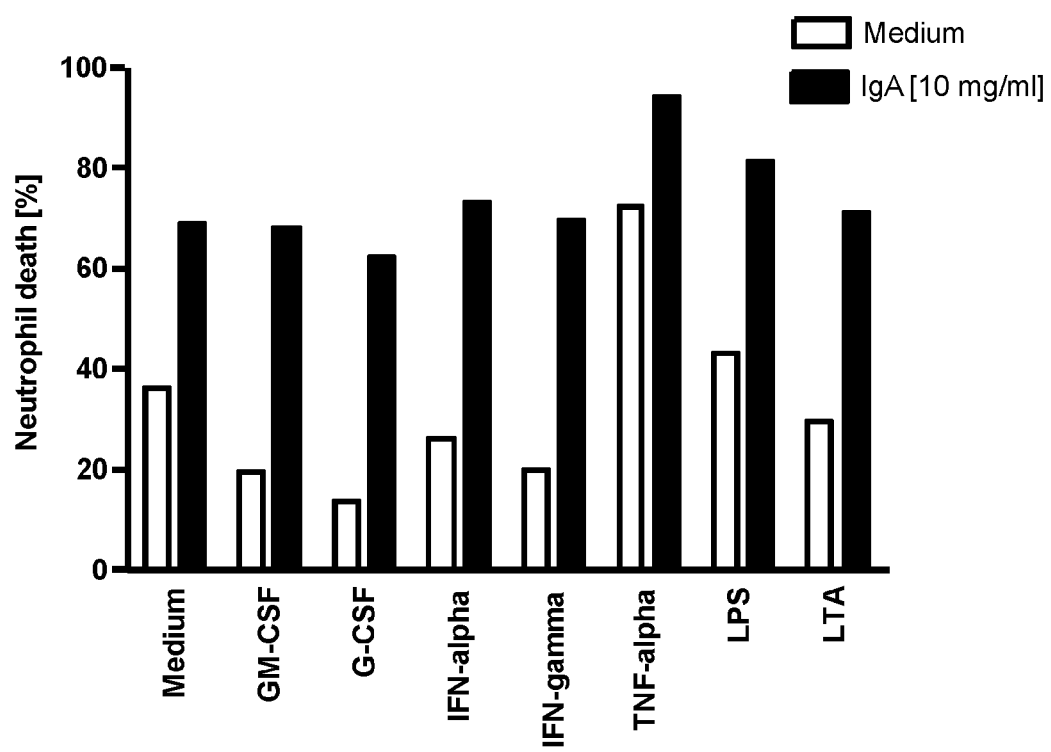
FIG. 3A shows neutrophil death of blood neutrophils isolated from healthy volunteers incubated with medium containing various inflammatory stimuli in the presence or absence of plasma IgA at 10mg/ml.

The invention is exemplified in the following examples. The examples are intended as an illustration of a way to perform the invention and are not supposed to be limiting the invention.

EXAMPLES Induction of Apoptosis in Neutrophils

Materials and Methods

Antibodies: Anti-CD89 (Clone A59) (both unlabeled and phycoerythrin [PE]-conjugated), and PE-conjugated immunoglobulin G1 (IgG1) isotype control were from BD Biosciences (Basel, Switzerland). Goat anti-mouse IgG (GaM) and unlabelled control IgG1 were obtained from Jackson ImmunoResearch Laboratories (distributed by Milan Analytica, La Roche, Switzerland). Anti-Fas agonistic mAb (CH11) was obtained from LabForce AG (Nunningen, Switzerland). Pooled serum IgA was obtained from CSL Behring AG (Wankdorf, Bern), and was prepared as follows: IgA was purified from human plasma and side-fraction of the IVIg/SCIg manufacturing process by affinity chromatography using CaptureSelect Human IgA resin from BAC (Naarden, Netherlands). Briefly, cryo-depleted human pool plasma or side-fraction was loaded onto an equilibrated CaptureSelect Human IgA column under near physiological conditions (pH, conductivity), without exceeding the IgA-binding capacity of the column. After loading the column was washed with phosphate buffered saline and IgA was eluted with a glycin buffer at pH 3. The eluates were pH-corrected and concentrated up to 50 mg/ml protein. Monomeric IgA can be purified from plasma IgA obtained as described above by preparative size-exclusion chromatography, for example using Superdex 200 gel resin. Cells: Blood neutrophils were isolated from healthy individuals as well as patients suffering from rheumatoid arthritis (RA) associated with acute joint inflammation. Briefly, peripheral blood mononuclear cells (PBMCs) were separated by centrifugation on Ficoll-Hypaque (Seromed-Fakola AG, Basel, Switzerland). The lower phase, mainly granulocytes and erythrocytes, was treated with erythrocyte lysis solution (155 mM $NH_4Cl$, 10 mM $KHCO_3$, and 0.1 mM EDTA [ethylenediaminetetraacetic acid], pH 7.3). The resulting cell populations contained mostly neutrophils. Joint fluid neutrophils from patients with RA were isolated using the same protocol. Cell purity was assessed by staining with Diff-Quik (Baxter, Düdingen, Switzerland) and light microscopy analysis. The purity of the resulting populations was at least 95% for neutrophils.

Immunofluorescence: CD89 surface expression was analyzed by flow cytometry following incubation of the cells with saturating concentrations of PE-conjugated anti-CD89 and isotype-matched PE-conjugated control mAbs.

Cell Cultures: Neutrophils were cultured at $1 \times 10^6$/mL in the presence or absence of cytokines or LPS and/or antibodies for the indicated times using complete culture medium (RPMI 1640 containing 10% fetal calf serum [FCS] and 200 IU/mL penicillin/100 µg/mL streptomycin, all from Life Technologies, Basel, Switzerland). If not indicated otherwise, cells were stimulated with 17.5 µg/mL anti-CD89 mAb or with 10 mg/ml plasma IgA. GM-CSF (Novartis Pharma GmbH, Nürnberg, Germany) was used at 25 ng/mL, anti-Fas mAb (CH11) at 1 µg/mL. LPS (Sigma Aldrich, Buchs, Switzerland) was used at 100 ng/ml. Goat anti-mouse was used at 30 µg/ml, G-CSF (Aventis Pharma, Zurich, Switzerland) at 25 ng/mL, IFN-γ (R&D Systems, Wiesbaden-Nordenstadt, Germany) at 85 ng/mL, IFN-α (PBL Biomedical Laboratories, distributed by Alexis) at 500 U/mL, TNF-α (R&D Systems, Wiesbaden-Nordenstadt, Germany) at 25 ng/mL, and LTA (Gift from T. Hartung University of Konstanz) at 10 µg/mL. The caspase inhibitor qVD-OPh (quinoline-Val-Asp-difluorophenoxymethylketone) was used at 20

Determination of Cell Death and Apoptosis: Cell death was assessed by uptake of 1 µM ethidium bromide and flow cytometric analysis (FACSCalibur, Becton Dickinson). To determine the form of cell death, morphologic analysis and annexin V analysis were performed. For morphologic analysis, the cells were cultured for 15 hours, and stained with Giemsa-May-Grünwald (Diff-Quik). An Axiovert 35 microscope equipped with a 630/1.4 oil objective lens was used (Carl Zeiss, Heidelberg, Germany). Images were processed with Adobe Photoshop 5.0 software (Adobe, San Jose, Calif.). To determine whether cell death was apoptosis, redistribution of phosphatidylserine (PS) on the neutrophil's membrane was measured by Annexin V staining and flow cytometry (FACSCalibur, Becton Dickinson), using a commercially available apoptosis detection kit according to the manufacturer's protocol (BD Biosciences), in the presence of propidium iodide (PI) (von Gunten S et al., Blood 2005; 106:1423-1431). To detect DNA fragmentation, a typical hallmark of apoptosis, the cells were permeabilized by a hypotonic fluorochrome solution (50 µg/ml Propidium iodide, 0.1% Sodium citrate, 0.1% Triton X-100), leading to a leakage of DNA multimers (182 bp) out of the cell. The remaining, reduced amount of DNA was then stained by the DNA intercalating agent propidium iodide and analyzed by flow cytometry (Nicoletti I et al., J. Immunol. Methods 1991; 139:271-279).

Statistical Analysis: Statistical analysis was performed by using the Student t test. If mean levels are presented, the standard error of the mean (SEM) and the number (n) of independent experiments are indicated in each case. A probability value of less than 0.05 was considered statistically significant.

Example 1

CD89 Expression on Neutrophils Upon Stimulation with LPS or GM-CSF

Neutrophils were isolated from blood of healthy volunteers as described above. The cells were incubated in the presence or absence of inflammatory stimulus (100 ng/ml LPS or 10 ng/ml GM-CSF) for 8 hours. The cells were then incubated with phycoerythrin (PE)-labeled anti-CD89 or PE-labeled isotype-matched control antibody. CD89 expression was then assessed by flow cytometry.

Neutrophils expressed CD89 in the absence of inflammatory stimulus (FIG. 1A), and CD89 expression was increased when the cells were incubated in the presence of an inflammatory stimulus such as LPS (FIG. 1A, left panel) or GM-CSF (FIG. 1A, right panel). The profiles of the cells stained with the control antibody are also shown.

FIG. 1B shows the time course of CD89 upregulation with LPS and GM-CSF. Significant upregulation of expression was observed after 4 hours.

Example 2

CD89 Ligation Stimulates Neutrophil Cell Death

Neutrophils were isolated as described above. The cells were then incubated with anti-CD89 monoclonal antibody, anti-Fas antibody, anti-Fas+anti-CD89, each in the presence and absence of goat-anti mouse antibody (GaM). Cell death was assessed by ethidium bromide uptake and flow cytometric analysis. Ligation of CD89 by an anti-CD89 monoclonal antibody (mAb) resulted in significantly increased neutrophil cell death (FIG. 2A), similar to anti-Fas induced cell death. CD89-mediated death was further significantly enhanced by crosslinking. Results of 22-hour cultures are shown (n=5). (B) A concentration effect curve of anti-CD89 mAb in 22-hour neutrophil cultures indicated maximal death effects at 17.5 µg/ml (n=5) (FIG. 2B).

IgA isolated from plasma or monoclonal IgA, and other Fc-alpha-comprising molecules will show similar effects, in particular if cross-linking of CD89 is achieved.

Example 3

Serum IgA and CD89 Induce Neutrophil Cell Death

Blood neutrophils were isolated from healthy volunteers as described above. The cells were incubated with medium in the presence or absence of plasma IgA at 10 mg/ml (FIG. 3A) or anti-CD89 mAb at 17.5 µg/ml (FIG. 3B) in the presence of various inflammatory stimuli. IgA clearly increased cell death in activated neutrophils (FIG. 3A).

Figure 3B:
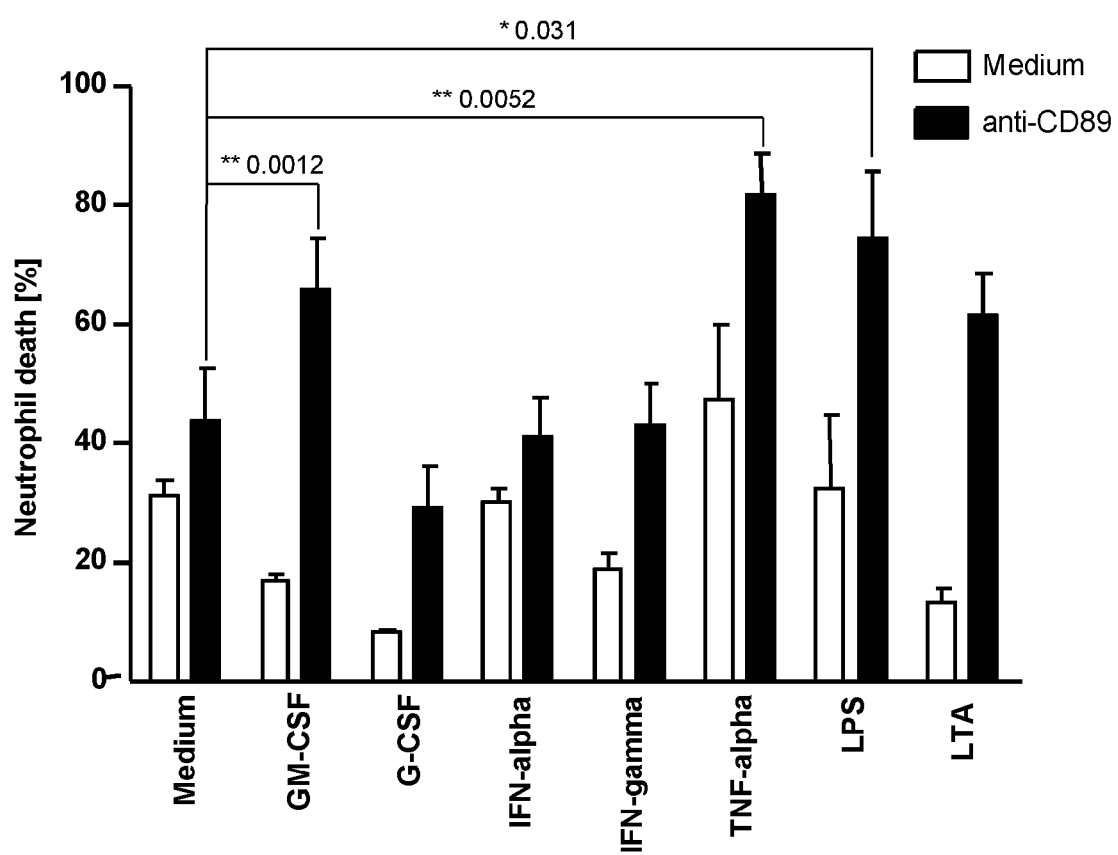
FIG. 3B shows neutrophil death of blood neutrophils isolated from healthy volunteers incubated with medium containing various inflammatory stimuli in the presence or absence of anti-CD89 mAb at 17.5μg/ml.
Figure 3C:
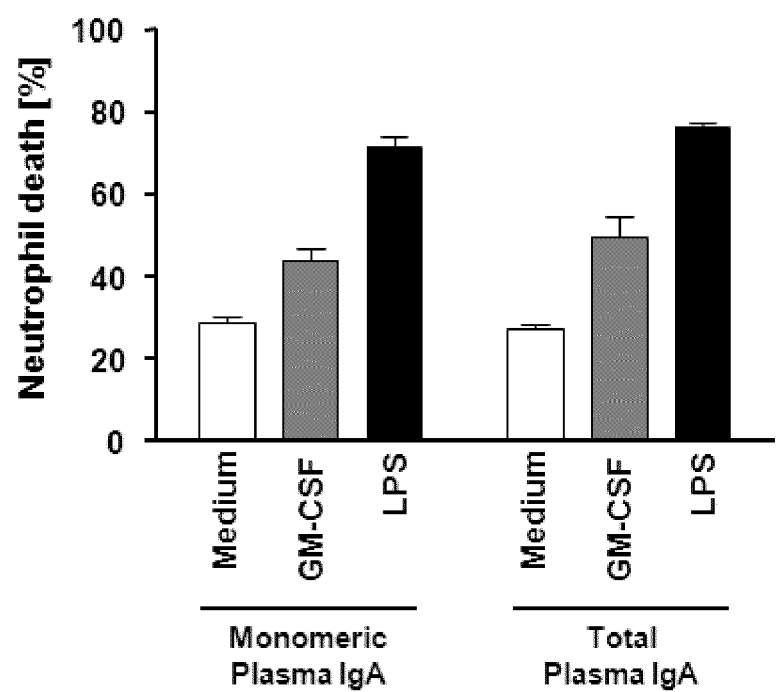
FIG. 3C shows total plasma IgA and monomeric subfraction plasma IgA effectiveness in inducing neutrophil cell death in the presence or absence of GM-CSF and LPS.

Similar results were obtained with anti-CD89 monoclonal antibody, shown in FIG. 3B. Total plasma IgA (containing monomers and dimers) and a monomeric subfraction of plasma IgA were equally effective in inducing neutrophil cell death (FIG. 3C).

Example 4

Neutrophils from Ankylosing Spondyloarthritis Patients Express Enhanced Levels of CD89

Figure 4:
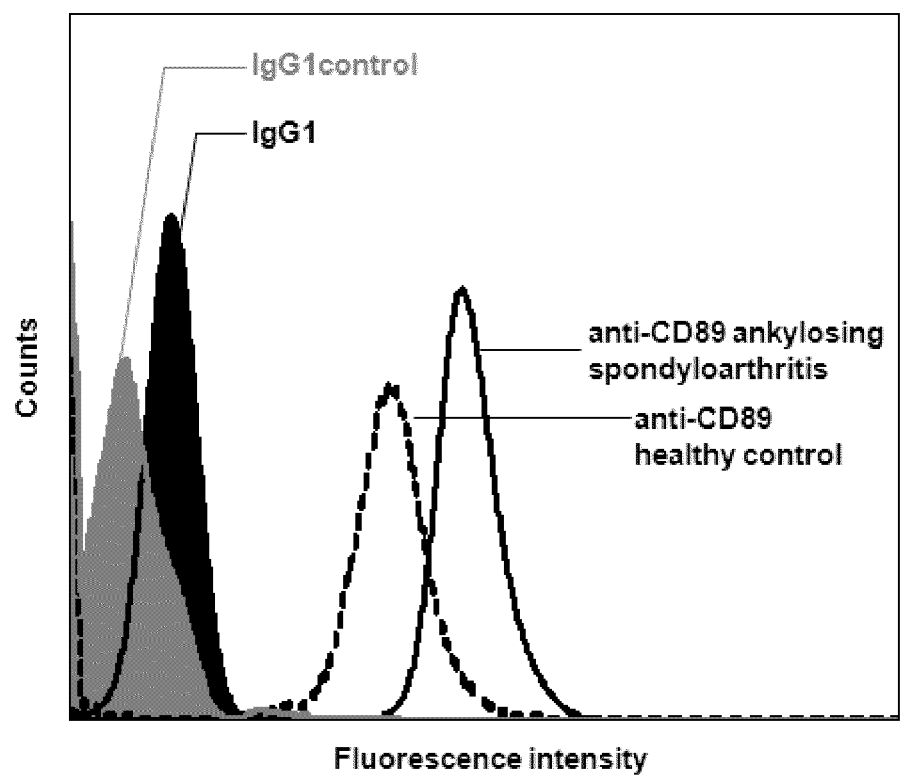
FIG. 4 shows CD89 expression analyzed by flow cytometry of isolated neutrophils from blood of healthy volunteers and an ankylosing spondyloarthritis patient incubated with PE-labeled anti-CD89 mAb or PE-labeled control antibody.

Neutrophils were isolated from blood of a healthy volunteer and of an ankylosing spondyloarthritis patient. They were then incubated with PE-labeled anti-CD89 mAb or PE-labeled control antibody and CD89 expression was analyzed by flow cytometry. The neutrophils from the ankylosing spondyloarthritis patient showed significantly increased surface expression of CD89 (FIG. 4, solid line) compared to the healthy donor (FIG. 4, dotted line). Staining with isotype-matched control mAb of the same samples of neutrophils is also shown.

Example 5

Figure 5A:
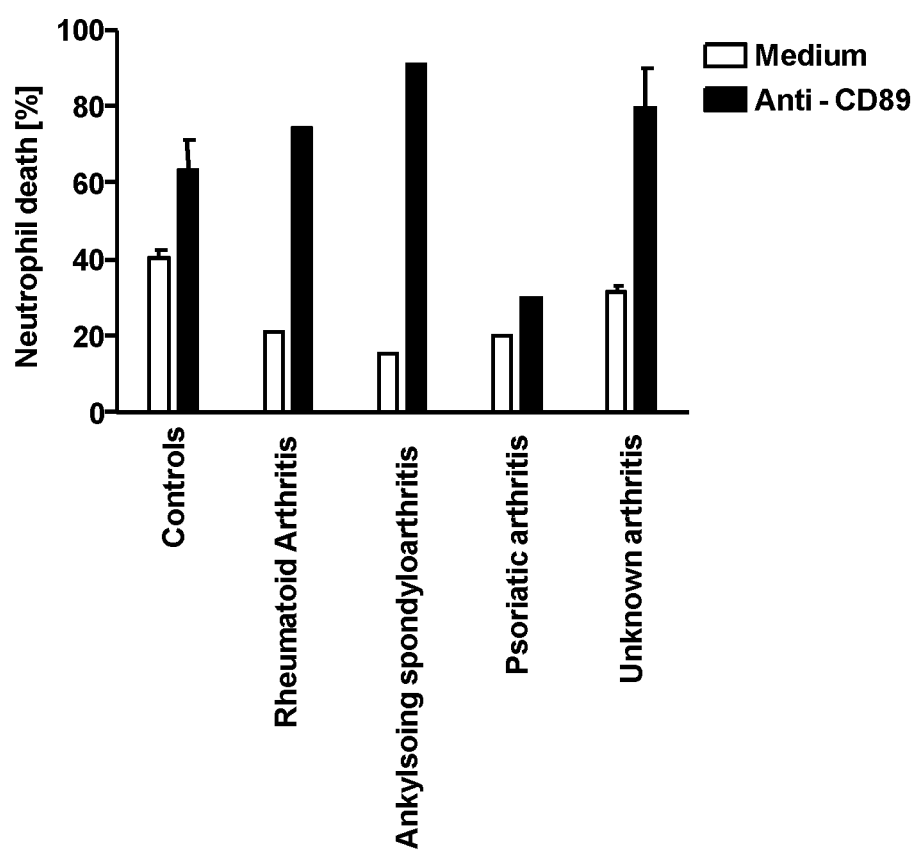
FIG. 5A shows neutrophil death in the presence of anti-CD89 antibody in joint/synovial fluid neutrophils from rheumatoid arthritis, ankylosing spondyloarthritis, psoriatric arthritis, and "unknown" arthritis patients as compared to control neutrophils isolated from the blood of healthy volunteers.
Figure 5B:
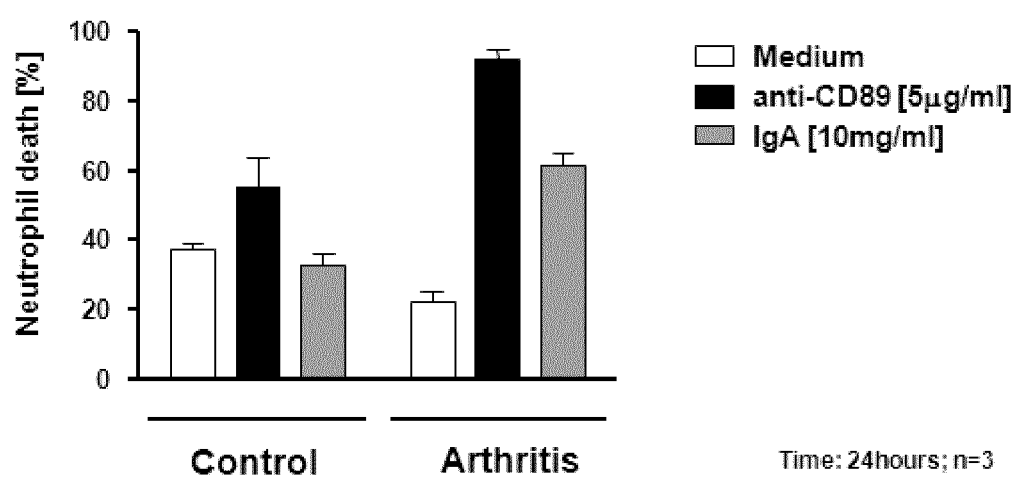
FIG. 5B shows neutrophil death in the presence of IgA in joint/synovial fluid neutrophils from arthritis patients as compared to control neutrophils isolated from the blood of healthy volunteers.

Neutrophils Isolated from Patients are More Susceptible to Anti-CD89- and IgA-Mediated Cell Death Neutrophils were isolated from blood of healthy volunteers for control purposes, and from joint/synovial fluid of arthritis patients (patients suffering from rheumatoid arthritis, ankylosing spondyloarthritis, psoriatric arthritis and "unknown" arthritis), and were cultured for 24 hours in presence or absence of anti-CD89 antibody or medium; thereafter neutrophil cell death was analyzed as described above. Anti-CD89 led to a high rate of death in synovial neutrophils from arthritis patients. The death rate was significantly higher than that of neutrophils from blood of healthy volunteers as shown in FIG. 5A. The same effect was observed with plasma IgA at 10 mg/ml (FIG. 5B).

Example 6

Pan-Caspase Inhibitor qVD-OPh Inhibits IgA-Mediated Cell Death in Neutrophils

Figure 6:
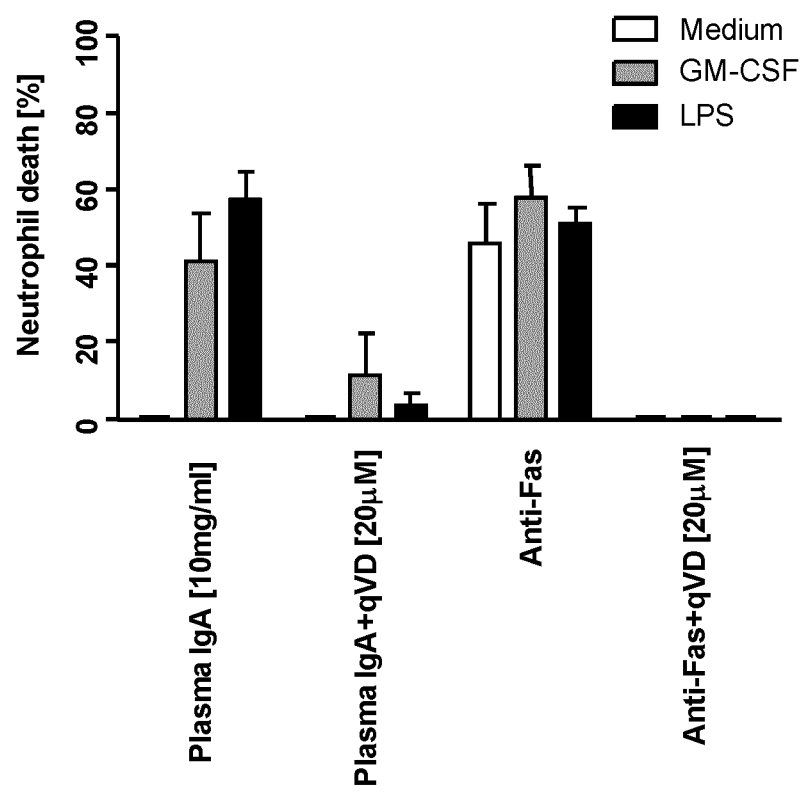
FIG. 6 shows neutrophil death of neutrophils isolated from healthy volunteer blood cultured in the presence or absence of inflammatory stimulus in the presence of IgA, pan-caspase inhibitor qVD, anti-Fas mAb and anti-Fas mAb+qVD.

Neutrophils were isolated from blood from healthy volunteers as described above. The cells were then cultured for 24 hours in the presence or absence of inflammatory stimulus (LPS, GM-CSF), and cell death in the absence or presence of IgA and/or pan-caspase inhibitor qVD-OPh (20 µM) was assessed. The results are shown in FIG. 6. The pan caspase-inhibitor qVD-OPh blocked the plasma IgA-mediated neutrophil cell death both in the presence and absence of LPS and GM-CSF. As a control apoptosis induction with an anti-Fas mAb and its inhibition with qVD-OPh is shown. These findings indicate that IgA-mediated neutrophil cell death is caspase-dependent programmed cell death, i.e. apoptosis.

Example 7

Phosphatidyl Serine Redistribution Upon Pooled Serum IgA Binding to Neutrophils, as Shown by Annexin V Staining Neutrophils were isolated from blood of healthy volunteers as described above, and incubated in medium, medium with GM-CSF or LPS, in the presence or absence of plasma IgA or anti-CD89 mAb. For control neutrophils were incubated with an apoptosis-inducing anti-Fas mAb. After 6 hours, the phosphatidyl serine distribution was assessed by Annexin V staining and flow cytometry. After 10 hours the DNA fragmentation was assessed by propidium iodine staining and flow cytometry.

Figure 7A:
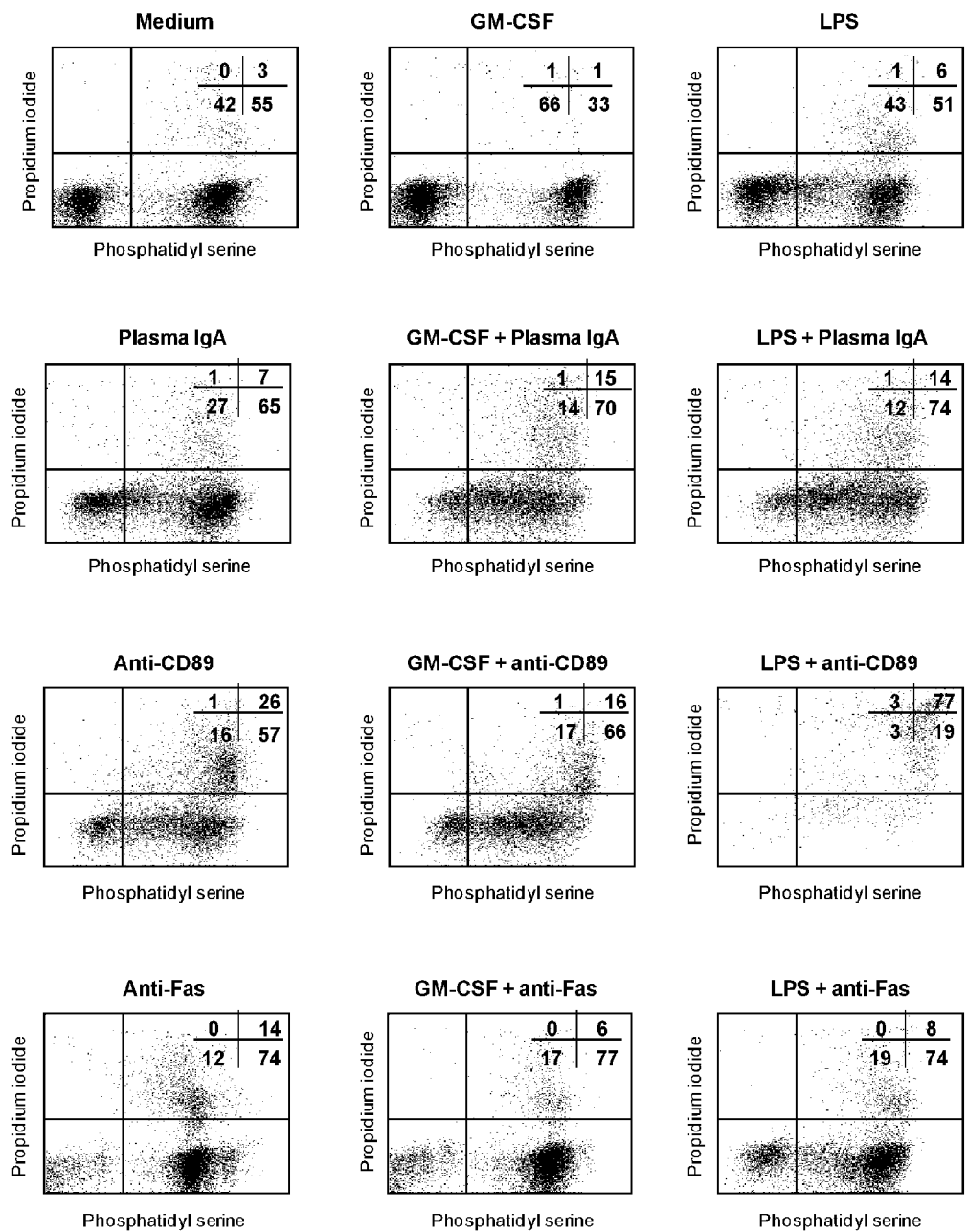
FIG. 7A shows phosphatidyl serine distribution assessed by staining and flow cytometry of neutrophils isolated from healthy volunteer blood induced in medium with GM-CSF or LPS in the presence or absence of IgA or anti-CD89 mAb.
Figure 7B:
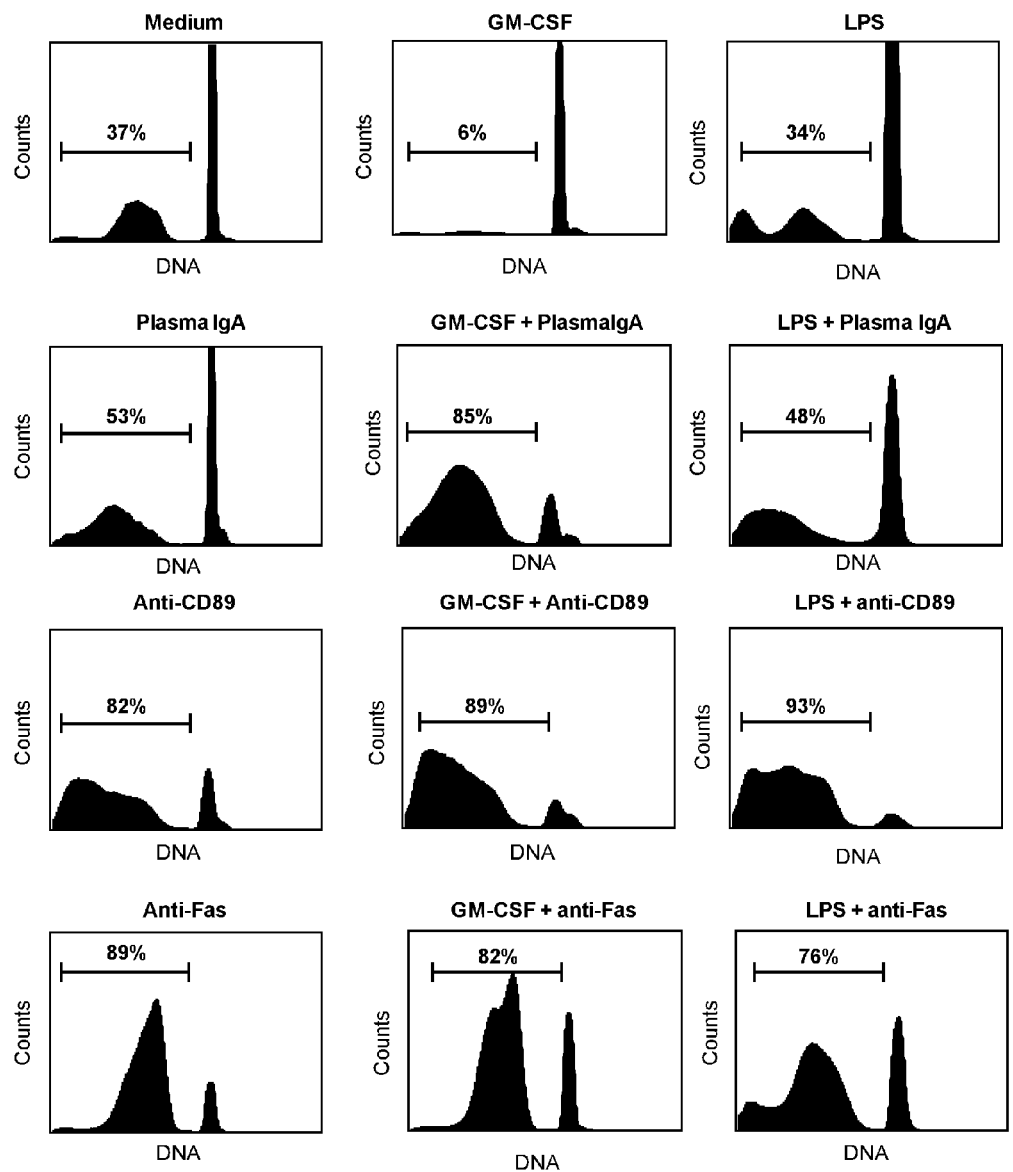
FIG. 7B shows DNA fragmentation assessed by staining and flow cytometry of neutrophils isolated from healthy volunteer blood induced in medium with GM-CSF or LPS in the presence or absence of IgA or anti-CD89 mAb.

Pooled serum IgA ligation in presence of GM-CSF or LPS resulted in strong phosphatidyl-serine redistribution (FIG. 7A) and DNA fragmentation (FIG. 7B), both indicative for the induction of neutrophil apoptosis. Comparable results were obtained using anti-CD89 mAb instead of plasma IgA (FIG. 7A, 7B). These scatter plots show one representative experiment out of 5. Percentages of cells in each quadrant are indicated. In FIG. 7B, the relative number of apoptotic cells (percentage) is indicated in each histogram.

Example 8

Morphology of CD89-Mediated Neutrophil Death

Neutrophils were isolated from blood from healthy volunteers as described above. They were cultured for 15 hours in the presence of medium alone, GM-CSF, or LPS, in the presence and absence of anti-CD89. They were stained with Giemsa-May-Grünwald (Diff-Quik), and examined by microscopy. CD89-mediated neutrophil death showed the typical morphological features of classic apoptosis (reduced cell volume, fragmented nuclei). IgA-mediated neutrophil death is expected to show the same morphology.

The invention claimed is:

1. A method for treating an autoimmune disorder or an inflammatory condition in a patient associated with excessive neutrophil infiltration by inducing apoptosis of neutrophils, comprising:
    administering to the patient having an autoimmune disorder or an inflammatory condition associated with excessive neutrophil infiltration an effective dose of a soluble CD89-activating molecule, which is a soluble Fc-alpha comprising molecule or a functional variant thereof, to bring neutrophils in contact with said molecule thereby causing apoptosis,
    wherein the effective dose provides a local concentration of said soluble CD89-activating molecule at a site of excessive neutrophil infiltration which is at least about three times the IgA plasma concentration.

2. The method of claim 1, wherein the neutrophils have been pre-activated by an inflammatory stimulus selected from the group consisting of inflammatory cytokines and microbial components.

3. The method of claim 1, wherein the soluble CD89-activating molecule comprises Fc-alpha.

4. The method of claim 3, wherein the soluble Fc-alpha comprising molecule is immunoglobulin A (IgA).

5. The method of claim 4, wherein the IgA is derived from serum or plasma.

6. The method of claim 4 or 5, wherein the IgA is dimeric.

7. The method of claim 4 or 5, the effective dose containing an effective dose of IgA that is monomeric.

8. The method of claim 6, wherein the IgA dimer comprises a J-chain.

9. The method of claim 8, wherein the IgA dimer comprises a secretory component.

10. The IgA of claim 4 or 5, wherein the IgA comprises monomeric and dimeric IgA.

11. The method of claim 4 or 5, wherein the IgA is polyclonal.

12. The method of claim 4, wherein the IgA is monoclonal.

13. The method claim 4, wherein the IgA is IgA1 or IgA2 or a mixture thereof.

14. The method of claim 1, wherein the CD89-activating molecule is administered as part of a pharmaceutical composition comprising the CD89-activating molecule, wherein at least 50% of the protein in the composition is the CD89-activating molecule.

15. The method of claim 1, wherein the neutrophils are comprised in a patient with an autoimmune disorder.

16. The method of claim 15, wherein the autoimmune disorder or inflammatory condition is selected from sterile neutrophilic inflammation, infectious inflammation, neutrophil-induced inflammation, inflammatory bowel disease and NETosis.

17. The method of claim 15, wherein the autoimmune disorder is arthritis.

18. The method according to claim 1, wherein the neutrophils are in a patient with cystic fibrosis.

19. The method of claim 17, wherein the arthritis is rheumatoid arthritis, spondyloarthritis, ankylosing spondylitis/Morbus Bechterew, or reactive arthritis.

20. A method for treating an autoimmune disorder or an inflammatory condition by inducing apoptosis of neutrophils, comprising:
  administering to a patient having an autoimmune disorder or an inflammatory condition an effective dose of a soluble CD89-activating molecule, which is a soluble Fc-alpha comprising molecule or a functional variant thereof, to bring neutrophils in contact with said molecule thereby causing apoptosis, and
  observing neutrophil apoptosis in the patient's neutrophils after administering the effective dose of the soluble CD89-activating molecule.

21. The method of claim 1, wherein said effective dose is administered topically.

22. A method for treating an autoimmune disorder or an inflammatory condition in a patient associated with excessive neutrophil infiltration by inducing apoptosis of neutrophils, comprising:
  administering to a patient having an autoimmune disorder or an inflammatory condition associated with excessive neutrophil infiltration an effective dose of a soluble CD89-activating molecule, which is a soluble Fc-alpha comprising molecule or a functional variant that is not IgA having a secretory component, to bring neutrophils in contact with said molecule thereby causing apoptosis,
  wherein the neutrophils have been pre-activated by an inflammatory stimulus,
  wherein the CD89-activating molecule is administered locally to provide the effective dose of a local concentration of said soluble CD89-activating molecule at a site of excessive neutrophil infiltration or activity which is at least about three times the IgA plasma concentration.

23. The method of claim 22, wherein said effective dose is administered topically.

24. A method for treating an autoimmune disorder or an inflammatory condition by inducing apoptosis of neutrophils, comprising:
  administering to a patient having an autoimmune disorder or an inflammatory condition an effective dose of a soluble CD89-activating molecule, which is a soluble Fc-alpha comprising molecule or a functional variant that is not IgA having a secretory component, to bring neutrophils in contact with said molecule thereby causing apoptosis,
  wherein the neutrophils have been pre-activated by an inflammatory stimulus,
  wherein the CD89-activating molecule is administered locally to provide the effective dose of a local concentration of said soluble CD89-activating molecule at a site of excessive neutrophil infiltration or activity which is at least about three times the IgA plasma concentration,
  wherein said effective dose is administered into a diseased joint of an arthritis patient.

25. The method of claim 24, wherein said arthritis patient is a rheumatoid arthritis patient.

26. The method of claim 22, wherein said effective dose is administered to a site of a sterile or infectious inflammation.

27. The method of claim 22, wherein said effective dose is administered to the site of a chronic neutrophilic inflammation.

28. The method of claim 1, wherein said soluble CD89-activiating molecule is substantially free of secretory component.

29. The method of claim 22, wherein said soluble CD89-activiating molecule is substantially free of secretory component.

30. The method of claim 22, wherein said local concentration of said CD89-activiating molecule is at least about 10 times the IgA plasma concentration.

31. The method of claim 22, wherein said local concentration of said CD89-activiating molecule is at least about 20 times the IgA plasma concentration.

* * * * *